US012527909B2

(12) United States Patent
Han

(10) Patent No.: US 12,527,909 B2
(45) Date of Patent: Jan. 20, 2026

(54) APPARATUS FOR INFUSING MEDICAL LIQUID

(71) Applicant: IPV, Seoul (KR)

(72) Inventor: Yongjoon Han, Seoul (KR)

(73) Assignee: IPV, Seoul (KR)

( * ) Notice: Subject to any disclaimer, the term of this patent is extended or adjusted under 35 U.S.C. 154(b) by 590 days.

(21) Appl. No.: 17/637,678

(22) PCT Filed: Aug. 25, 2020

(86) PCT No.: PCT/KR2020/011321
§ 371 (c)(1),
(2) Date: Feb. 23, 2022

(87) PCT Pub. No.: WO2022/045386
PCT Pub. Date: Mar. 3, 2022

(65) Prior Publication Data
US 2024/0325630 A1 Oct. 3, 2024

(51) Int. Cl.
*A61M 5/142* (2006.01)
*A61M 5/145* (2006.01)
*A61M 5/158* (2006.01)

(52) U.S. Cl.
CPC ...... *A61M 5/14248* (2013.01); *A61M 5/1452* (2013.01); *A61M 2005/1585* (2013.01)

(58) Field of Classification Search
CPC ............ A61M 5/14248; A61M 5/1452; A61M 5/158; A61M 25/0612; A61M 5/3129; A61M 2005/1585; A61M 2005/3131; A61M 2005/3151
USPC .................................................... 604/19, 230
See application file for complete search history.

(56) References Cited

U.S. PATENT DOCUMENTS 4,437,858 A * 3/1984 Ty ........................ A61M 5/3129 604/90
8,900,205 B2 12/2014 Ishii
9,782,542 B2 10/2017 Conzone et al.
(Continued)

FOREIGN PATENT DOCUMENTS

EP 3 708 137 A1 9/2020
KR 10-2008-0104570 A 12/2008
(Continued)

OTHER PUBLICATIONS

Gang, Dispoable Syringe Which Can Put Drug Into with a Fixed Quantity, KR_20080104570_A English translation and original document (Year: 2008).*
(Continued)

*Primary Examiner* — James D Ponton
*Assistant Examiner* — John A Doubrava
(74) *Attorney, Agent, or Firm* — Knobbe, Martens, Olson & Bear, LLP

(57) ABSTRACT

An apparatus for infusing medical liquid, the apparatus including: a needle module having at least one needle portion formed to be injected into a user's body; a medical liquid storage portion having an inner space to store medical liquid delivered to the needle module, wherein an inner surface of the inner space includes a surface-treated shape; and a driving portion connected to the medical liquid storage portion to transfer the medical liquid of the medical liquid storage portion to the needle module.

5 Claims, 18 Drawing Sheets

(56) References Cited

U.S. PATENT DOCUMENTS

| | | | | |
|---|---|---|---|---|
| 2005/0236063 A1* | 10/2005 | DiGregorio | A61M 5/3129 | 141/18 |
| 2009/0093793 A1* | 4/2009 | Gross | A61M 5/14566 | 604/218 |
| 2010/0057014 A1* | 3/2010 | Cane | A61M 5/31515 | 604/222 |
| 2010/0305513 A1* | 12/2010 | Araki | B29C 45/00 | 604/221 |
| 2016/0022913 A1* | 1/2016 | Creaturo | A61M 5/31511 | 604/189 |

FOREIGN PATENT DOCUMENTS

| | | | |
|---|---|---|---|
| KR | 20080104570 A | * | 12/2008 |
| KR | 10-1161570 B1 | | 7/2012 |
| KR | 10-2019-0026730 A | | 3/2019 |
| KR | 10-2021-0012312 A | | 2/2021 |
| WO | WO 2005/108242 A1 | | 11/2005 |
| WO | WO 2011/156373 A1 | | 12/2011 |
| WO | WO 2018/041708 A1 | | 3/2018 |
| WO | WO 2019/021906 A1 | | 7/2020 |

OTHER PUBLICATIONS

International Search Report issued for International Patent Application No. PCT/KR2020/011321, dated May 17, 2021 in 3 pages.

Written Opinion issued for International Patent Application No. PCT/KR2020/011321, dated May 17, 2021 in 4 pages.

Extended European Search Report dated Aug. 9, 2022 in Application No. 20947810.6, 9 pages.

Office Action dated Jul. 18, 2022 in Korean Application No. 10-2021-0063417.

Notice of Allowance dated May 24, 2023 in Korean Application No. 10-2021-0063417.

Office Action dated Nov. 28, 2023 in Korean Application No. 10-2023-0112233.

* cited by examiner

APPARATUS FOR INFUSING MEDICAL LIQUID

CROSS-REFERENCE TO RELATED APPLICATIONS

This application is the U.S. National Phase under 35. U.S.C. § 371 of International Application PCT/KR2020/011321, filed Aug. 25, 2020. The disclosure of the above-described application is hereby incorporated by reference in its entirety.

BACKGROUND

Field

Embodiments of the present disclosure relate to an apparatus for infusing medical liquid.

Description of the Related Art

An apparatus for infusing medical liquid, such as an apparatus for infusing insulin, is used to infuse medical liquid into a patient's body, which is sometimes used by medical professionals such as doctors and nurses, but is in most cases used by the general public, such as the patient himself or a caregiver. And, since the medical liquid infused through the apparatus for infusing medical liquid is often taken by the patient for a long time, the patient experiences pain of inserting a needle of the apparatus for infusing medical liquid several times.

This apparatus for infusing medical liquid has the needle from which the medical liquid is discharged, and may infuse the medical liquid into the patient's body once or multiple times, after the needle is injected into the patient's body.

On the other hand, in order to increase the effect through the infusion of the medical liquid, the apparatus for infusing medical liquid needs to be controlled to precisely infuse the medical liquid into the patient's body, but there is a limit to precisely infusing a small amount of medical liquid through the apparatus for infusing medical liquid, for example, to precisely infusing the medical liquid sequentially more than once.

SUMMARY OF CERTAIN INVENTIVE ASPECTS

Embodiments of the present disclosure provides an apparatus for infusing medical liquid with improved precise medical liquid infusion control characteristics.

An embodiment of the present disclosure discloses an apparatus for infusing medical liquid, the apparatus including a needle module having at least one needle portion formed to be injected into a user's body; a medical liquid storage portion having an inner space to store medical liquid delivered to the needle module, wherein an inner surface of the inner space includes a surface-treated shape; and a driving portion connected to the medical liquid storage portion to transfer the medical liquid of the medical liquid storage portion to the needle module.

In this embodiment, the medical liquid storage portion may include an outer portion defining one region of the inner space, the outer portion may include an outer surface and a medical liquid facing region facing the outer surface, and the surface-treated shape may be formed in the medical liquid facing region.

In this embodiment, the inner surface of the inner space of the medical liquid storage portion and an outer surface of the medical liquid storage portion may be formed to have different surface shapes.

In this embodiment, a roughness value of the inner surface of the inner space of the medical liquid storage portion may be different from a roughness value of the outer surface of the medical liquid storage portion.

In this embodiment, the roughness value of the inner surface of the inner space of the medical liquid storage portion may be greater than the roughness value of the outer surface of the medical liquid storage portion.

In this embodiment, the inner surface of the inner space of the medical liquid storage portion may be formed to include a plurality of protrusions and spaces.

In this embodiment, the apparatus may further include a cover portion formed to cover the medical liquid storage portion, the needle module and the driving portion.

Other aspects, features and advantages other than those described above will become apparent from the following detailed description of the drawings, claims and disclosure.

An apparatus for infusing medical liquid according to the present embodiment may improve precise medical liquid infusion control characteristics.

DETAILED DESCRIPTION OF CERTAIN ILLUSTRATIVE EMBODIMENTS

Figure 1:
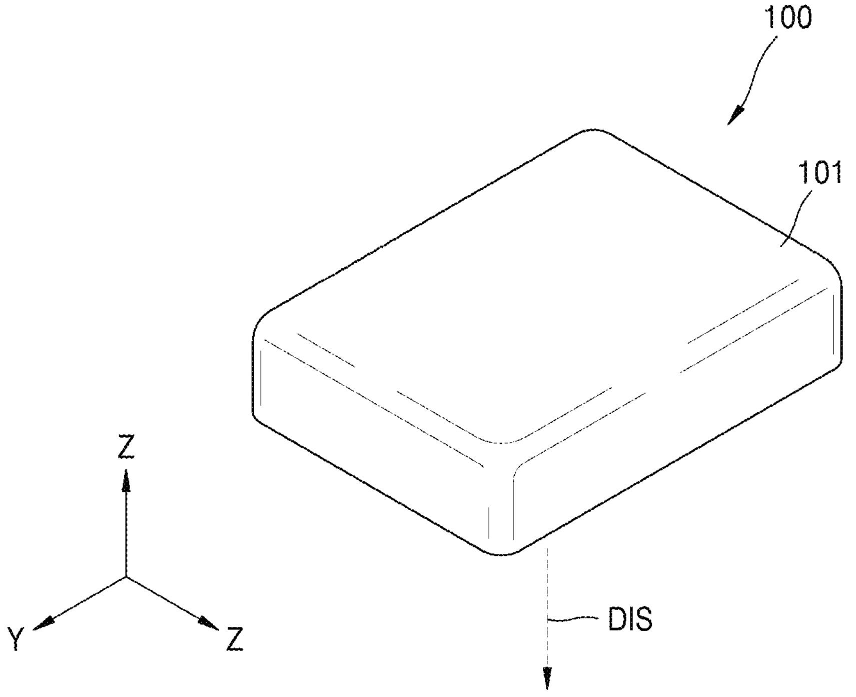
FIG. 1 is a perspective view schematically illustrating an apparatus for infusing medical liquid according to an embodiment of the present disclosure.

Since the present disclosure may apply various transformations and may have various embodiments, specific embodiments are illustrated in the drawings and described in detail in the detailed description. Effects and features of the present disclosure, and a method of achieving them will become apparent with reference to the embodiments described below in detail in conjunction with the drawings. However, the present disclosure is not limited to the embodiments disclosed below and may be implemented in various forms.

Hereinafter, embodiments of the present disclosure will be described in detail with reference to the accompanying drawings, and when described with reference to the drawings, the same or corresponding components are given the same reference numerals, and the overlapping description thereof will be omitted.

In the following embodiments, terms such as first, second, etc. are used for the purpose of distinguishing one component from another, not in a limiting sense.

In the following examples, the singular expression includes the plural expression unless the context clearly dictates otherwise.

In the following embodiments, terms such as include or have means that the features or components described in the specification are present, and the possibility that one or more other features or components will be added is not excluded in advance.

In the drawings, the size of the components may be exaggerated or reduced for convenience of description. For example, since the size and thickness of each component shown in the drawings are arbitrarily indicated for convenience of description, the present disclosure is not necessarily limited to what is illustrated.

In the following embodiments, the x-axis, y-axis, and z-axis are not limited to three axes on a Cartesian coordinate system, and may be interpreted in a broad sense including them. For example, the x-axis, y-axis, and z-axis may be orthogonal to each other, but may refer to different directions that are not orthogonal to each other.

In cases where certain embodiments may be implemented otherwise, a specific process sequence may be performed different from the described sequence. For example, two processes described in succession may be performed substantially simultaneously, or may be performed in an order opposite to the order described.

Figure 2:
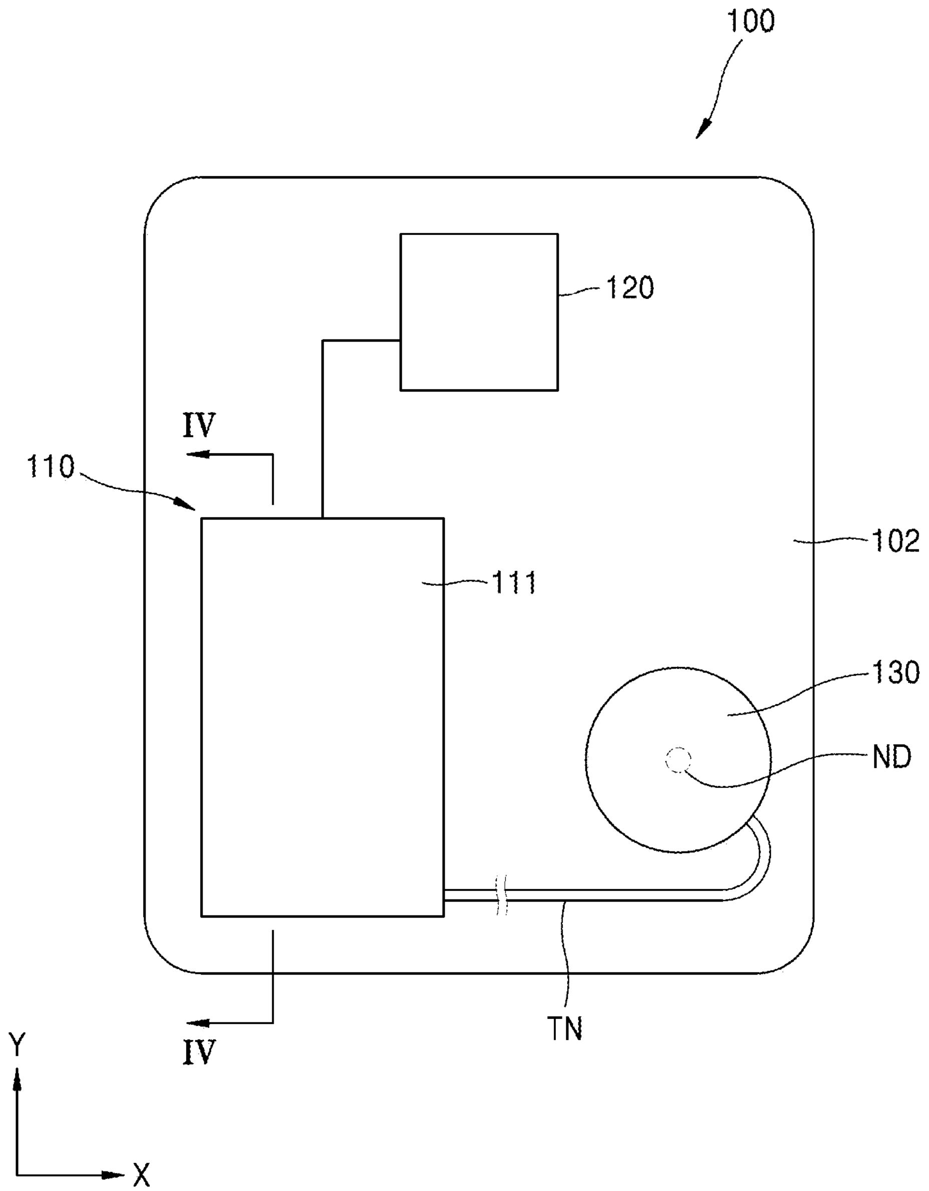
FIG. 2 is a schematic plan view of the apparatus for infusing medical liquid of FIG. 1.
Figure 3:
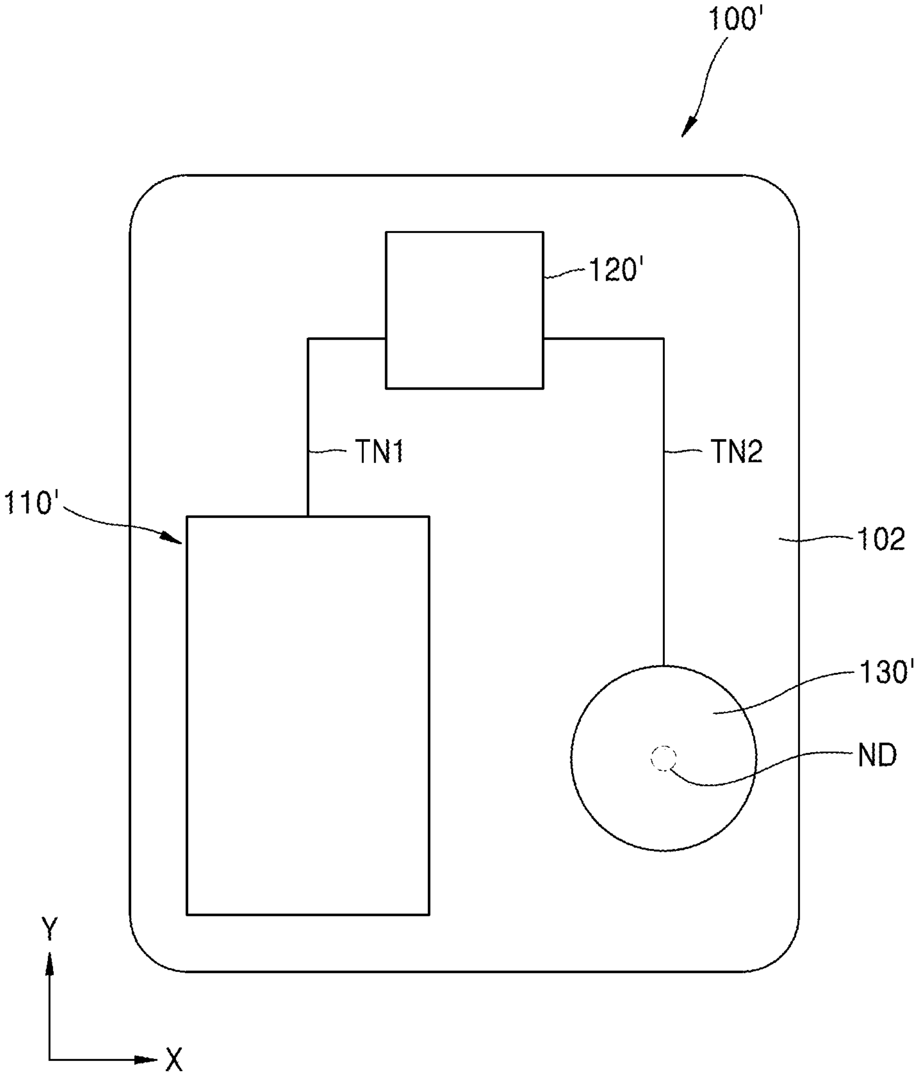
FIG. 3 is a diagram illustrating a modified example of FIG. 2.

FIG. 1 is a perspective view schematically illustrating an apparatus for infusing medical liquid according to an embodiment of the present disclosure, FIG. 2 is a schematic plan view of the apparatus for infusing medical liquid of FIG. 1, and FIG. 3 is a diagram illustrating a modified example of FIG. 2.

Figure 4:
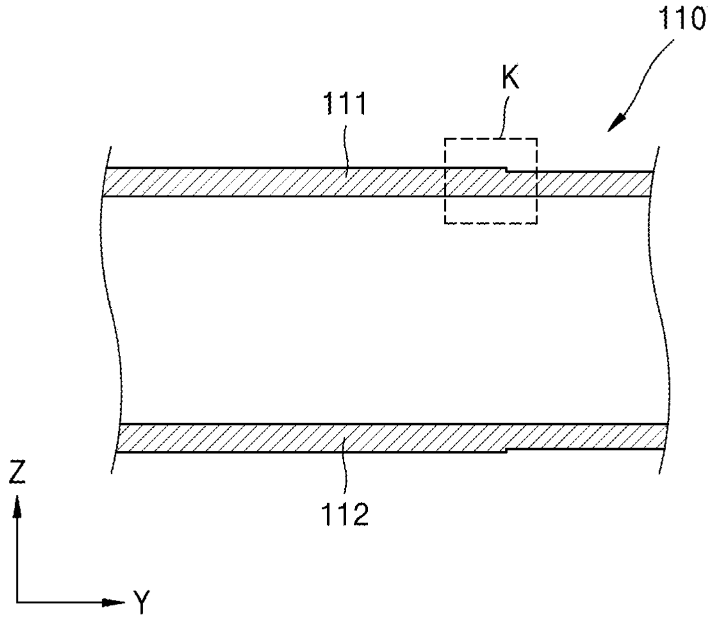
FIG. 4 is a cross-sectional view taken along line IV-IV of FIG. 2.
Figure 5:
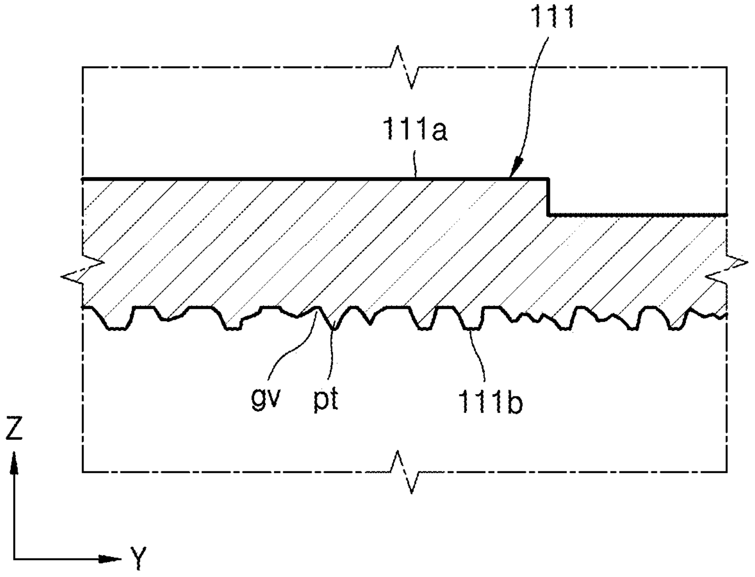
FIG. 5 is an enlarged view of K of FIG. 4.

FIG. 4 is a cross-sectional view taken along line IV-IV of FIG. 2, and FIG. 5 is an enlarged view of K of FIG. 4.

Referring to FIGS. 1 and 2, an apparatus for infusing medical liquid 100 of this embodiment may include a medical liquid storage portion 110, a driving portion 120, and a needle module 130.

The apparatus for infusing medical liquid 100 may be disposed adjacent to a medical liquid infusion target, for example, a human skin, and may infuse the medical liquid in an infusion direction DIS.

Also, as an optional embodiment, the apparatus for infusing medical liquid 100 may be mounted on a user's body.

The apparatus for infusing medical liquid 100 may include a cover 101, and the cover 101 may be formed to cover the medical liquid storage portion 110, the driving portion 120 and the needle module 130.

For convenience of explanation, FIG. 2 illustrates a state in which the cover 101 of FIG. 1 is removed.

Referring to FIG. 2, the apparatus for infusing medical liquid 100 may include a base 102, and the base 102 may be formed to face the cover 101.

In an optional embodiment, the cover 101 and the base 102 may be connected to each other to become a housing of the apparatus for infusing medical liquid 100.

Although not illustrated, as an optional embodiment, the cover 101 may include an opening, a button is disposed to correspond to the opening, and the button may correspond to the needle module 130. The button corresponding to the needle module 130 is formed so that the user may press or rotate it, and movement with respect to the needle module 130 may be possible through the button.

The medical liquid storage portion 110 may be formed to accommodate one or more types of medical liquids. For example, the medical liquid storage portion 110 may accommodate a medical liquid to infuse the medical liquid into a human at one time. Also, as another example, the medical liquid storage portion 110 may accommodate a medical liquid to continuously infuse the medical liquid over a plurality of times.

The medical liquid storage portion 110 may include a tank-shaped container to store the medical liquid. The medical liquid storage portion 110 may contain a waterproof material, for example, a plastic-based material, capable of accommodating the medical liquid, and may be formed of various other materials.

As an alternative embodiment, the medical liquid storage portion 110 may contain a glass, metal, or silicon material.

As illustrated in FIG. 2, the medical liquid storage portion 110 includes at least one outer portion 111, and the medical liquid may be accommodated in an inner space formed inside the outer portion 111. For example, the outer portion 111 may be a first outer portion 111 facing the cover 101.

The medical liquid may be of various types, and may include an insulin-based medical liquid for diabetic patients, other medical liquids for pancreas, cardiac medical liquid, and other various types of medical liquid.

In an alternative embodiment, the medical liquid storage portion 110 may be replenished with the medical liquid through a charging passage (not illustrated).

In addition, although not illustrated, the medical liquid storage portion 110 may include at least one moving portion (not illustrated) in the space in which the medical liquid is accommodated inside the outer portion 111, such the moving portion may allow the medical liquid to move effectively, and specifically, may allow the medical liquid accommodated in the medical liquid storage portion 110 to be easily delivered to the needle module 130 to be described later.

The space inside the first outer portion 111 of the medical liquid storage portion 110 will be described in more detail with reference to FIG. 4 to be described later.

The driving portion 120 may allow the medical liquid stored in the medical liquid storage portion 110 to be delivered to the needle module 130, and to be easily infused from the needle module 130 into the medical liquid infusion target, for example, human skin.

As an optional embodiment, the driving portion 120 may include a pump, and the medical liquid stored in the medical liquid storage portion 110 may be delivered to the needle module 130 by a predetermined amount through pumping of the pump.

Although not illustrated, the driving portion 120 may be connected to a power source.

Also, as an optional embodiment, the driving portion 120 may be electrically connected to a controller (not illustrated), and the driving portion 120 may control infusion of the medical liquid through the control of the controller.

All kinds of pumps having a medical liquid suction power and a medical liquid discharge power by electricity may be used for the driving portion 120. For example, all kinds of pumps such as mechanical displacement type micropump and electromagnetic motion type micropump may be used. The mechanical displacement type micropump is a pump that uses the motion of a solid or fluid, such as a gear or diagram, to generate a pressure difference to induce the flow of fluid, and includes a diaphragm displacement pump, a fluid displacement pump, a rotary pump, and the like. The electromagnetic motion type micropump is a pump that directly uses electrical or magnetic energy to move a fluid, and includes a hydrodynamic pump (EHD), an electro osmotic pump, a magneto hydrodynamic pump, an electro wetting pump, and the like.

The needle module 130 may include at least one needle portion ND. The needle portion ND has an empty interior, and the medical liquid of the medical liquid storage portion 110 may be infused into the medical liquid infusion target through this interior space.

A connection portion TN may be disposed between the needle module 130 and a medical liquid storage portion 110. The connection portion TN may include a delivery region such that at least the medical liquid of the medical liquid storage portion 110 is delivered to the needle module 130, for example, may include a hollow tube shape.

The connection portion TN may be formed in various shapes, for example, may include a flexible tube shape.

The driving portion 120 of the present embodiment may be connected to the medical liquid storage portion 110 so that the medical liquid accommodated in the medical liquid storage portion 110 may be easily delivered to the needle module 130 through the connection portion TN.

Also, although not illustrated, as an optional embodiment, a sensor (not illustrated) may be further positioned between the cover 101 and the base 102, or on at least one surface of them.

Such the sensor (not illustrated) may be provided to sense whether the needle module 130 is adjacent to a needle through hole formed in the base 102.

Also, such the sensor (not illustrated) may be electrically connected to the above-described controller (not illustrated) that controls the driving portion 120.

FIG. 3 is a diagram illustrating a modified example of FIG. 2.

Referring to FIG. 3, an apparatus for infusing medical liquid 100' may include a medical liquid storage portion 110', a driving portion 120' and a needle module 130'.

A first connection portion TN1 may be disposed between the medical liquid storage portion 110' and the driving portion 120', and the first connection portion TN1 may include a delivery region such that at least the medical liquid of the medical liquid storage portion 110' is delivered to the driving portion 120', for example, may include a hollow tube shape. The first connection portion TN1 may be formed in various shapes, for example, may include a flexible tube shape.

A second connection portion TN2 may be disposed between the driving portion 120' and the needle module 130', and the second connection portion TN2 may include a delivery region such that at least medical liquid is delivered from the driving portion 120' to the needle module 130', for example, may included a hollow tube shape. The second connection portion TN2 may be formed in various shapes, for example, may include a flexible tube shape.

FIG. 4 is a cross-sectional view taken along line IV-IV of FIG. 2, and FIG. 5 is an enlarged view of K of FIG. 4.

Referring to FIGS. 4 and 5, the inner space of the medical liquid storage portion 110 is illustrated. The inner space of the medical liquid storage portion 110 may be defined as an inner space of outer portion 111 and 112.

For example, the medical liquid storage portion 110 may include the first outer portion 111 and a second outer portion 112 facing each other.

The first outer portion 111 and the second outer portion 112 may be formed to face each other, for example, the first outer portion 111 may face the cover 101 and the second outer portion 112 may face the base 102.

The inner space is formed to face the first outer portion 111 and the second outer portion 112, and specifically, the inner space may be defined by inner surfaces corresponding to the first outer portion 111 and the second outer portion 112.

Referring to FIG. 5, the first outer portion 111 may include an outer surface region 111*a* and a medical liquid facing region 111*b*.

The outer surface region 111*a* may correspond to an outer surface of the first outer portion 111, and the medical liquid facing region 111*b* may define the inner space in which the medical liquid of the medical liquid storage portion 110 is accommodated, and may face the medical liquid at least in one region and contact the medical liquid at least at one time point.

The medical liquid facing region 111*b* may include a surface-treated region. As an optional embodiment, the medical liquid facing region 111*b* may include one or more protrusions pt and spaces gv adjacent thereto. For example, the medical liquid facing region 111*b* may include a plurality of protrusions pt, and spaces gv may be formed between adjacent protrusions pt.

As an optional embodiment, the protrusion pt may include a plurality of protrusions pt having different sizes and shapes.

The medical liquid facing region 111*b* has the surface-treated region, for example, the region including the plurality of protrusions pt, so that when the medical liquid storage portion 110 is made of a material that transmits at least light, and when the medical liquid is accommodated in the medical liquid storage portion 110, a surface shape of the medical liquid facing region 111*b* may be recognized, and through this, it is possible to easily determine whether the medical liquid is accommodated or the accommodated amount.

In addition, the medical liquid facing region 111*b* may have the surface-treated region, for example, the region including the plurality of protrusions pt to increase the surface area so that the medical liquid is more efficiently accommodated in the medical liquid storage portion 110.

In addition, as an optional embodiment, when the moving portion for easy delivery of the medical liquid accommodated in the medical liquid storage portion 110 is included, the moving portion faces the surface-treated region of the medical liquid facing region 111*b*, for example the region including the plurality of protrusions pt, so that the friction force between the moving portion and the medical liquid facing region 111*b* is improved, the sliding of the moving portion is reduced or prevented, and effective and precise delivery of the medical liquid through the moving portion may be facilitated.

The protrusion pt may be formed in a fine shape so that unnecessary residual of the medical liquid is reduced, and damage or unnecessary interference to the moving portion that may be disposed therein is reduced.

For example, the size of the protrusion pt may be several micrometers or less, and specifically, it may be 0.1 to 10 micrometers.

Through this, the medical liquid facing region 111*b* may have a surface roughness value, for example, a roughness value of 0.1 to 5 micrometers, and specifically, a roughness value of 0.2 to 1 micrometers.

The medical liquid facing region 111*b* may be formed to include the plurality of protrusions pt by various methods, for example, may be formed by treating the surface by a physical method or may be formed by a method using a chemical solution.

As an optional embodiment, the outer surface region 111*a* and the medical liquid facing region 111*b* may have different surface shapes.

For example, the outer surface region 111*a* and the medical liquid facing region 111*b* may have different roughness. As a specific example, the outer surface region 111*a* and the medical liquid facing region 111*b* may have different surface roughness.

As an optional embodiment, the value of the surface roughness of the medical liquid facing region 111*b* may be greater than the value of the surface roughness of the outer surface region 111*a*.

Through this, the medical liquid storage portion 110 is formed of the material that transmits light, so that the surface characteristics of the medical liquid facing region 111*b* may be recognized, and whether the accommodated state and the accommodated amount of the stored medical liquid may be checked.

Although not illustrated, a medical liquid facing region of the second outer portion 112 opposite to the first outer portion 111 may also have a surface-treated region, for example, a plurality of protrusions, a detailed description is omitted because it is the same as that of the first outer portion 111.

Figure 6:
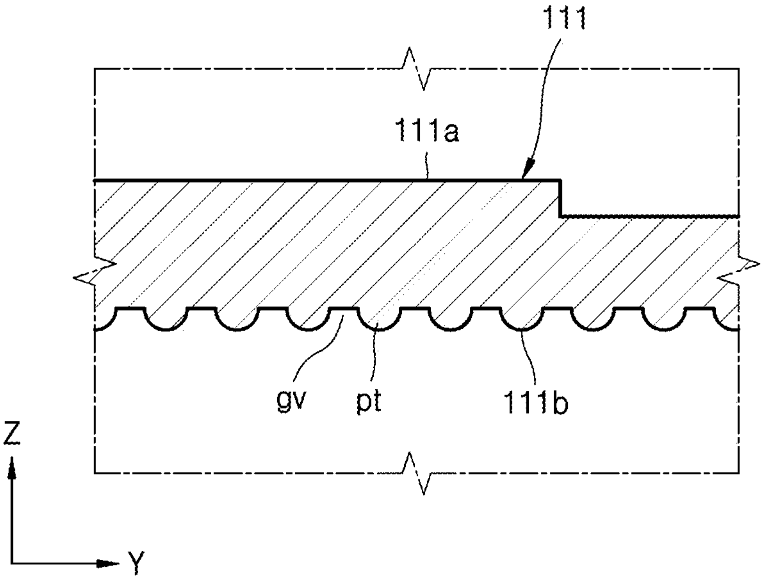
FIGS. 6 to 8 are views illustrating modified examples of FIG. 5.
Figure 7:
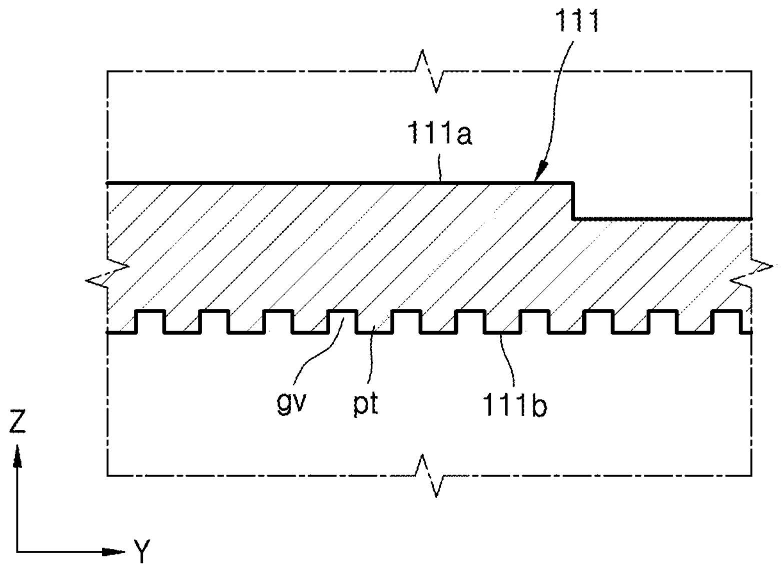
Figure 8:
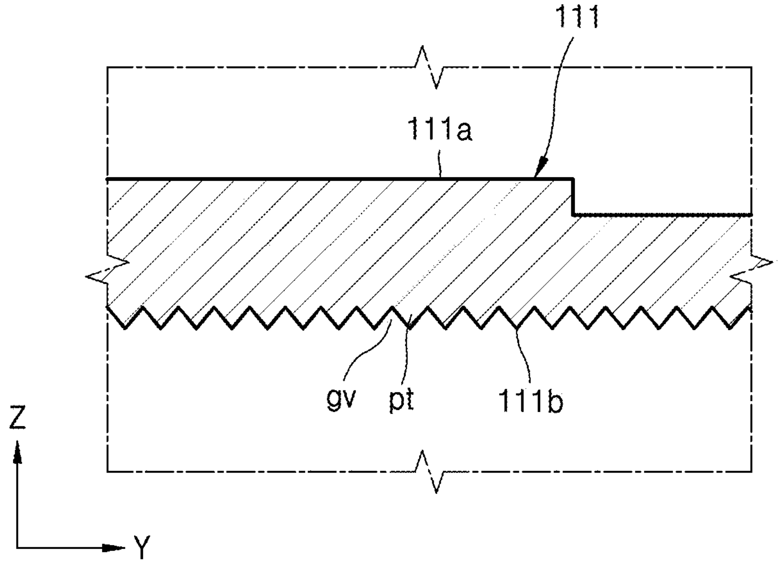

FIGS. 6 to 8 are views illustrating modified examples of FIG. 5.

Referring to FIG. 6, a medical liquid facing region 111*b* may include a surface-treated region. As an optional embodiment, the medical liquid facing region 111*b* may include one or more protrusions pt and spaces gv adjacent thereto. For example, the medical liquid facing region 111*b* may include a plurality of protrusions pt, and spaces gv may be formed between the protrusions pt adjacent to each other.

As an optional embodiment, the protrusion pt may include a curved surface. For example, the protrusion pt may have a spherical portion.

Through the protrusion pt of the curved surface, it is possible to realize the increase in effective friction force while reducing damage to the moving portion (not illustrated).

Referring to FIG. 7, a medical liquid facing region 111*b* may include a surface-treated region. As an optional embodiment, the medical liquid facing region 111*b* may include one or more protrusions pt and spaces gv adjacent thereto. For example, the medical liquid facing region 111*b* may include a plurality of protrusions pt, and spaces gv may be formed between the protrusions pt adjacent to each other.

As an alternative embodiment, the protrusion pt may include a plurality of protrusions pt having at least the same size and shape, and spaces gv having a uniform shape may be formed between the protrusion pt adjacent to each other.

In addition, as an optional embodiment, the protrusion pt may include a shape such as a column, and a cross-section may have a planar shape.

Referring to FIG. 8, a medical liquid facing region 111*b* may include a surface-treated region. As an optional embodiment, the medical liquid facing region 111*b* may include one or more protrusions pt and spaces gv adjacent thereto. For example, the medical liquid facing region 111*b* may include a plurality of protrusions pt, and spaces gv may be formed between the protrusions pt adjacent to each other.

As an optional embodiment, the protrusion pt may include a shape that decreases in width toward one end, for example, may include a cone, truncated cone, or sawtooth shape.

In this embodiment, the medical liquid is stored in the medical liquid storage portion of the apparatus for infusing medical liquid, and the medical liquid stored in the medical liquid storage portion may be delivered to the needle module through the driving portion, and may be infused into the infusion target, specifically, the user's body, over a plurality of times by a desired amount through pumping.

The medical liquid storage portion may include the outer portion, and the medical liquid may be accommodated in the inner space surrounded by the outer portion. The medical liquid facing region, which is the surface of the space facing the medical liquid of the outer portion, may include the protrusion and the space on the surface, for example, may include a region having roughness as it is finely surface-treated.

Through this, when the medical liquid storage portion is formed of the light-transmitting material, the presence or absence of medical liquid in the inner space, the remaining amount of the medical liquid, etc. may be easily checked through the shape of the surface of the medical liquid facing region. In addition, by increasing the surface area in contact with the medical liquid in the inner space of the medical liquid storage portion, it is possible to effectively accommodate the medical liquid in the medical liquid storage portion.

In addition, as an optional embodiment, the moving portion may be disposed in the medical liquid storage portion for pumping and moving the medical liquid, and the moving portion may include a piston shape. The medical liquid facing region of this embodiment may form a friction force with the moving portion and may reduce or prevent unnecessary sliding of the moving portion, so that the medical liquid of the medical liquid storage portion is effectively infused into the needle module, as a specific example, it is possible to precisely control the infusion of a predetermined medical liquid over a plurality of times.

Through this, it is possible to increase the convenience of the user who uses the apparatus for infusing medical liquid and the effect through infusion of the medical liquid.

Figure 9:
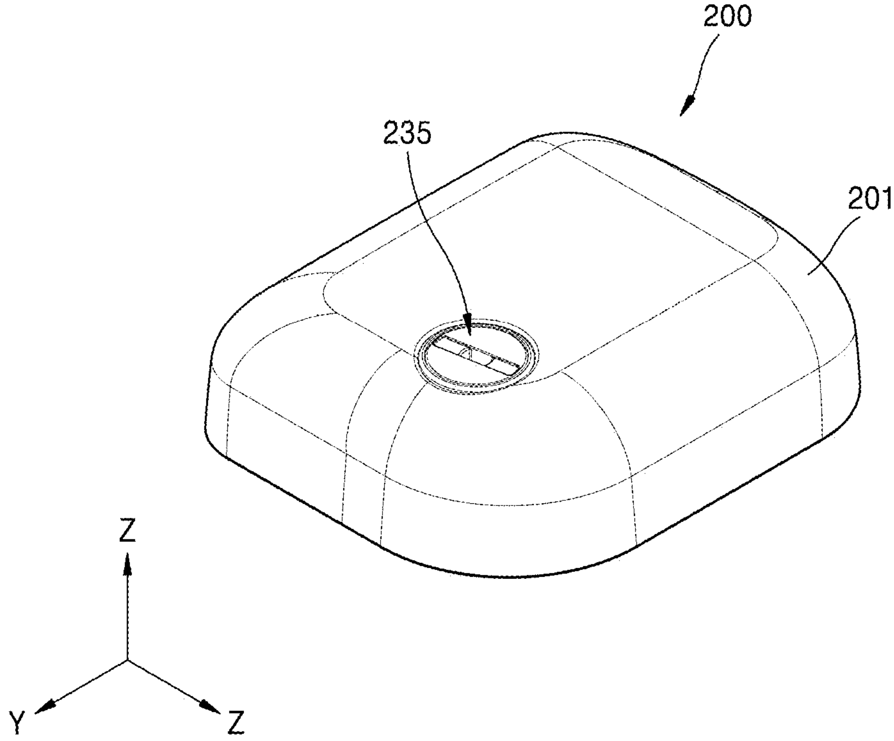
FIG. 9 is a perspective view schematically illustrating an apparatus for infusing medical liquid according to another embodiment of the present disclosure.
Figure 10:
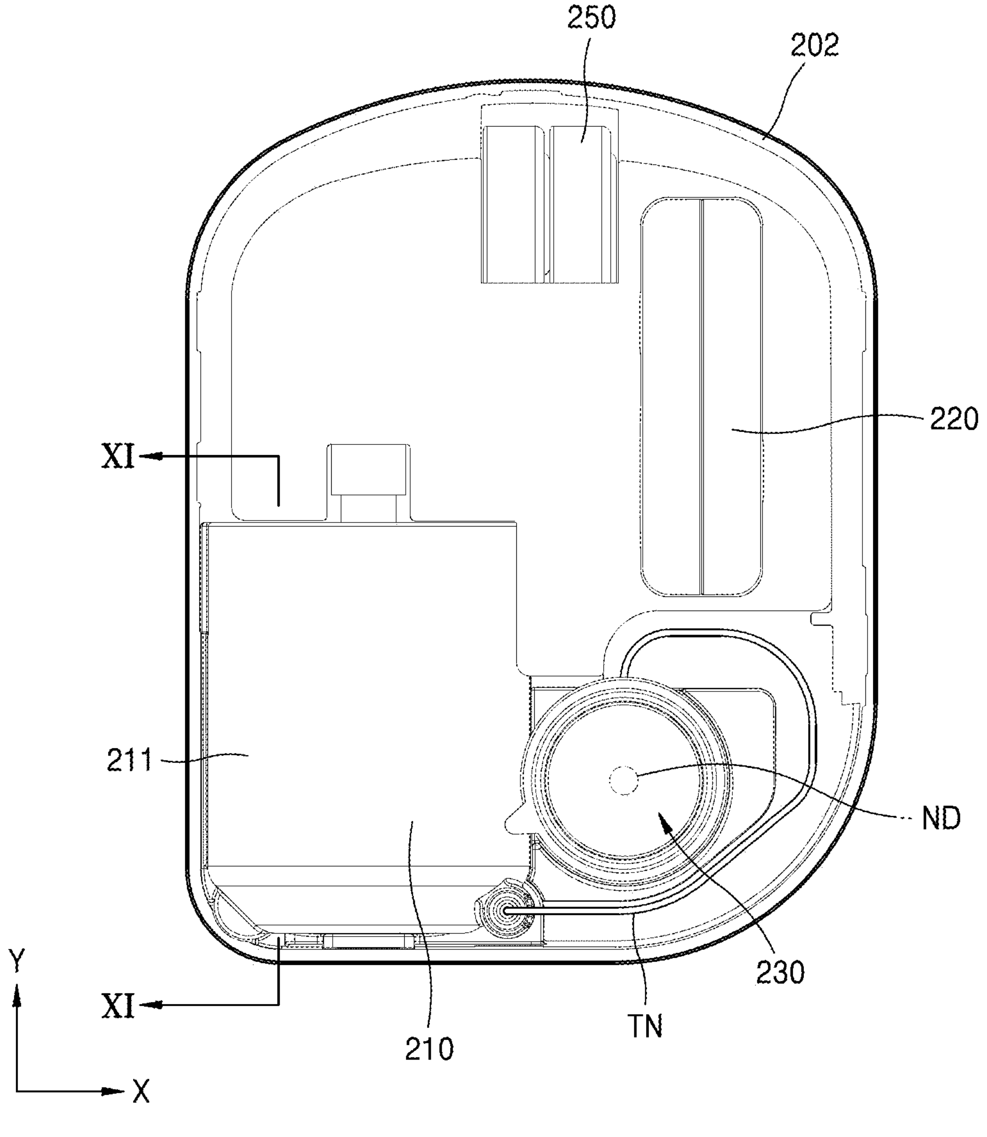
FIG. 10 is a schematic plan view of the apparatus for infusing medical liquid of FIG. 9.
Figure 11:
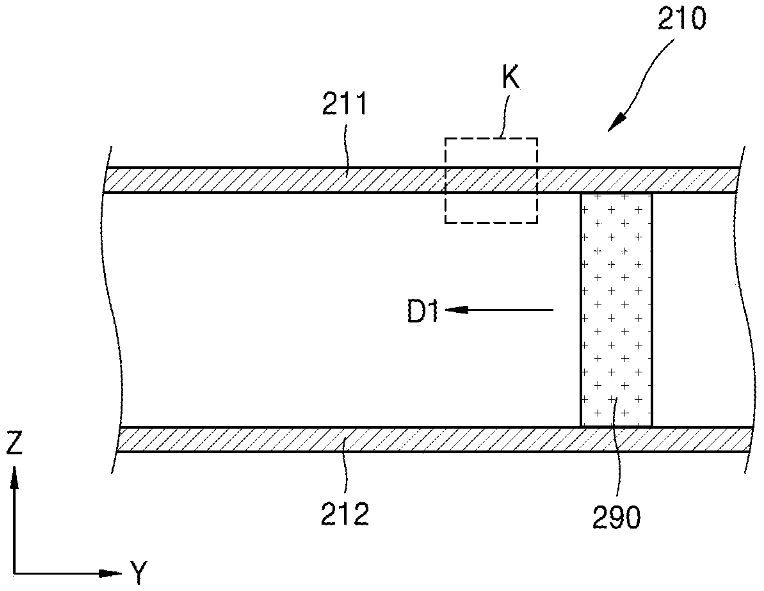
FIG. 11 is a cross-sectional view taken along line XI-XI of FIG. 10.
Figure 12:
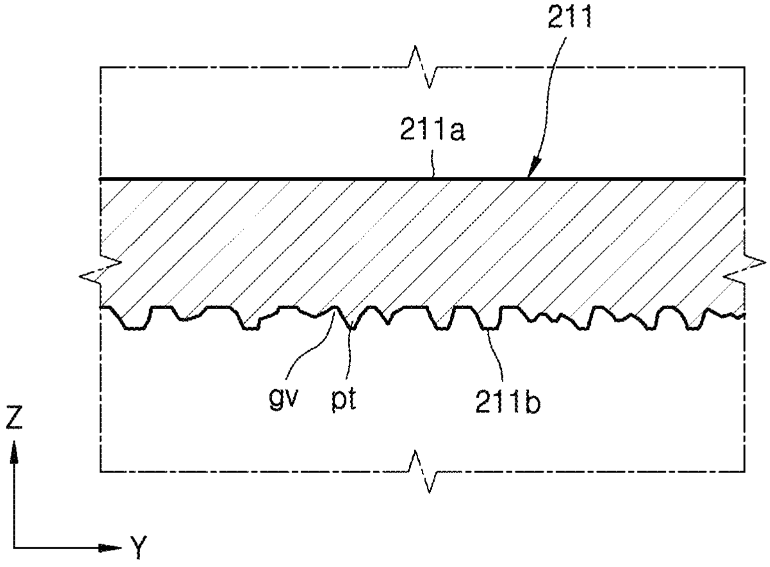
FIG. 12 is an enlarged view of K of FIG. 11.

FIG. 9 is a perspective view schematically illustrating an apparatus for infusing medical liquid according to another embodiment of the present disclosure, FIG. 10 is a schematic plan view of the apparatus for infusing medical liquid of FIG. 9, FIG. 11 is a cross-sectional view taken along line XI-XI of FIG. 10, and FIG. 12 is an enlarged view of K of FIG. 11.

Referring to FIGS. 9 to 12, an apparatus for infusing medical liquid 200 according to the present embodiment may include a medical liquid storage portion 210, a driving portion 220 and a needle module 230.

The apparatus for infusing medical liquid 200 may be disposed adjacent to a medical liquid infusion target, for example, a human skin, and may infuse the medical liquid in an infusion direction ('-' direction in Z-axis direction of FIG. 9).

Also, as an optional embodiment, the apparatus for infusing medical liquid 200 may be mounted on a user's body.

The apparatus for infusing medical liquid 200 may include a cover 201, and the cover 201 may be formed to cover the medical liquid storage portion 210, the driving portion 220 and the needle module 230.

For convenience of explanation, FIG. 10 illustrates a state in which the cover 201 of FIG. 9 is removed.

The apparatus for infusing medical liquid 200 may include a base 202, and the base 202 may be formed to face the cover 201.

As an optional embodiment, the cover 201 and the base 202 may be connected to each other to become a housing of the apparatus for infusing medical liquid 200.

As an optional embodiment, the cover 201 may include an opening, a button 235 is disposed to correspond to the opening, and the button 235 may correspond to the needle module 230.

For example, the button 235 may be disposed on the needle module 230, and the button 235 may be formed so that the user may press or rotate it. Movement with respect to the needle module 230 may be possible through the button 235.

The medical liquid storage portion 210 may be formed to accommodate one or more types of medical liquids. For example, the medical liquid storage portion 210 may accommodate a medical liquid to infuse the medical liquid into a human at one time. Also, as another example, the medical liquid storage portion 210 may accommodate a medical liquid to continuously infuse the medical liquid over a plurality of times.

The medical liquid storage portion 210 may include a tank-shaped container to store medical liquid. The medical liquid storage portion 210 may contain a waterproof material, for example, a plastic-based material, capable of accommodating the medical liquid, and may be formed of various other materials.

In an alternative embodiment, the medical liquid storage portion 210 may contain a glass, metal, or silicon material.

As illustrated in FIG. 10, the medical liquid storage portion 210 includes at least one outer portion 211, and the medical liquid may be accommodated in an inner space formed inside the outer portion 211. For example, the outer portion 211 may be a first outer portion 211 facing the cover 201.

The medical liquid may be of various types, and may include an insulin-based medical liquid for diabetic patients, other medical liquids for pancreas, cardiac medical liquid, and other various types of medical liquid.

As an optional embodiment, the medical liquid storage portion 210 may be replenished with the medical liquid through a charging passage (not illustrated).

A moving portion 290 may be disposed in the inner space of the medical liquid storage portion 210.

For example, at least one moving portion 290 may be disposed in a space in which the medical liquid is accommodated inside the outer portion 211 of the medical liquid storage portion 210.

Such the moving portion 290 may allow the medical liquid to move effectively, and specifically, may allow the medical liquid accommodated in the medical liquid storage portion 210 to be easily delivered to the needle module 230 to be described later.

For example, through the movement of the moving portion 290, the medical liquid stored in the medical liquid storage portion 210 may be infused into the user's body as many times as desired.

The space inside the first outer portion 211 of the medical liquid storage portion 210 will be described in more detail with reference to FIG. 12 to be described later.

The driving portion 220 may allow the medical liquid stored in the medical liquid storage portion 210 to be delivered to the needle module 230, and to be easily infused from the needle module 230 into the medical liquid infusion target, for example, human skin.

As an optional embodiment, the driving portion 220 may include a pump, and the medical liquid stored in the medical liquid storage portion 210 may be delivered to the needle module 230 by a predetermined amount through pumping of the pump.

The driving portion 220 may be connected to a power source 250. The power source 250 may include a battery, and may include a rechargeable battery. Also, as another example, the power source 250 may include a disposable battery.

Also, as an optional embodiment, the driving portion 220 may be electrically connected to a controller (not illustrated), and the driving portion 220 may control infusion of the medical liquid through the control of the controller.

All kinds of pumps having a medical liquid suction power and a medical liquid discharge power by electricity may be used for the driving portion 220. For example, all kinds of pumps such as mechanical displacement type micropump and electromagnetic motion type micropump may be used. The mechanical displacement type micropump is a pump that uses the motion of a solid or fluid, such as a gear or diagram, to generate a pressure difference to induce the flow of fluid, and includes a diaphragm displacement pump, a fluid displacement pump, a rotary pump, and the like. The electromagnetic motion type micropump is a pump that directly uses electrical or magnetic energy to move a fluid, and includes a hydrodynamic pump (EHD), an electro osmotic pump, a magneto hydrodynamic pump, an electro wetting pump, and the like.

The needle module 230 may include at least one needle portion ND. The needle portion ND has an empty interior, and the medical liquid of the medical liquid storage portion 210 may be infused into the medical liquid infusion target through this interior space.

A connection portion TN may be disposed between the needle module 230 and a medical liquid storage portion 210. The connection portion TN may include a delivery region such that at least the medical liquid of the medical liquid storage portion 210 is delivered to the needle module 230, for example, may include a hollow tube shape.

The connection portion TN may be formed in various shapes, for example, may include a flexible tube shape.

The driving portion 220 of the present embodiment may be connected to the medical liquid storage portion 210 so that the medical liquid accommodated in the medical liquid storage portion 210 may be easily delivered to the needle module 230 through the connection portion TN.

The needle module 230 may include a holder supporting the needle portion ND, and the holder supporting the needle portion ND may be disposed to face the button 235. Also, although not illustrated, a spring (not illustrated) may be disposed between the needle module 230 and the button 235. The button 235, spring (not illustrated), and the needle module 230 may be aligned along the Z-axis of FIG. 9.

Also, although not illustrated, as an optional embodiment, a sensor (not illustrated) may be further positioned between the cover 201 and the base 202, or on at least one surface of them.

Such the sensor (not illustrated) may be provided to sense whether the needle module 230 is adjacent to a needle through hole formed in the base 202.

Also, such the sensor (not illustrated) may be electrically connected to the above-described controller (not illustrated) that controls the driving portion 220.

FIG. 11 is a cross-sectional view taken along line XI-XI of FIG. 10, and FIG. 12 is an enlarged view of K of FIG. 11.

Referring to FIGS. 11 and 12, the inner space of the medical liquid storage portion 210 is illustrated. The inner space of the medical liquid storage portion 210 may be defined as an inner space of outer portion 211, 212.

For example, the medical liquid storage portion 210 may include the first outer portion 211 and a second outer portion 212 facing each other.

The first outer portion 211 and the second outer portion 212 may be formed to face each other, for example, the first outer portion 211 may face the cover 201 and the second outer portion 212 may face the base 202.

The inner space is formed to face the first outer portion 211 and the second outer portion 212, and specifically, the inner space may be defined by inner surfaces corresponding to the first outer portion 211 and the second outer portion 212.

The moving portion 290 may be disposed in the inner space corresponding to the first outer portion 211 and the second outer portion 212.

The moving portion 290 may have a piston shape and may include a column shape having a cross-sectional area. For example, the moving portion 290 may be formed in a cylindrical shape. Alternatively, the moving portion may have various shapes such as an elliptical pole shape or a polygonal pole shape such as a square pole. Specifically, the moving portion 290 may have a shape corresponding to the inner space of the medical liquid storage portion 210.

The moving portion 290 may move toward a discharge port (not illustrated) along the longitudinal direction D1 of the medical liquid storage portion 210 in the inner space of the medical liquid storage portion 210, and this discharge port (not illustrated) may be connected to the needle module 230.

The moving portion 290 moves in a state of being in contact with at least one region of the inner surface of the medical liquid storage portion 210, and the medical liquid stored in the inner space may be discharged to an outside of the medical liquid storage portion 210 through the discharge port (not illustrated) according to the movement of the moving portion 290. The moving portion 290 may include a material such as rubber and/or silicon. As an alternative embodiment, an elastic portion such as a rubber ring may be disposed in one region of an outer surface of the moving portion 290.

Referring to FIG. 12, the first outer portion 211 may include an outer surface region 211*a* and a medical liquid facing region 211*b*.

The outer surface region 211*a* may correspond to an outer surface of the first outer portion 211, and the medical liquid facing region 211*b* may define the inner space in which the medical liquid of the medical liquid storage portion 210 is accommodated, and may face the medical liquid at least in one region and contact the medical liquid at least at one time point.

The medical liquid facing region 211*b* may include a surface-treated region. As an optional embodiment, the medical liquid facing region 211*b* may include one or more protrusions pt and spaces gv adjacent thereto. For example, the medical liquid facing region 211*b* may include a plurality of protrusions pt, and spaces gv may be formed between adjacent protrusions pt.

As an optional embodiment, the protrusion pt may include a plurality of protrusions pt having different sizes and shapes.

The medical liquid facing region 211*b* has the surface-treated region, for example, the region including the plurality of protrusions pt, so that when the medical liquid storage portion 210 is made of a material that transmits at least light, and when the medical liquid is accommodated in the medical liquid storage portion 210, a surface shape of the medical liquid facing region 211*b* may be recognized, and through this, it is possible to easily determine whether the medical liquid is accommodated or the accommodated amount.

In addition, the medical liquid facing region 211*b* may have the surface-treated region, for example, the region including the plurality of protrusions pt to increase the surface area so that the medical liquid is more efficiently accommodated in the medical liquid storage portion 210.

In addition, the friction force and adhesion between the moving portion 290 for easy delivery of the medical liquid accommodated in the medical liquid storage portion 210 and the medical liquid facing region 211*b* may be improved.

Through this, when the moving portion 290 moves, the medical liquid may be effectively delivered from the medical liquid storage portion 210 to the needle module 230 as precisely as desired.

The protrusion pt may be formed in a fine shape so that unnecessary residual of the medical liquid is reduced, and damage or unnecessary interference to the moving portion 290 that may be disposed therein is reduced.

For example, the size of the protrusion pt may be several micrometers or less, and specifically, it may be 0.1 to 10 micrometers.

Through this, the medical liquid facing region 211*b* may have a surface roughness value, for example, a roughness value of 0.1 to 5 micrometers, and specifically, a roughness value of 0.2 to 1 micrometers.

The medical liquid facing region 211*b* may be formed to include the plurality of protrusions pt by various methods, for example, may be formed by treating the surface by a physical method or may be formed by a method using a chemical solution.

As an optional embodiment, the outer surface region 211*a* and the medical liquid facing region 211*b* may have different surface shapes.

For example, the outer surface region 211*a* and the medical liquid facing region 211*b* may have different roughness. As a specific example, the outer surface region 211*a* and the medical liquid facing region 211*b* may have different surface roughness.

As an optional embodiment, the value of the surface roughness of the medical liquid facing region 211*b* may be greater than the value of the surface roughness of the outer surface region 211*a*.

Through this, the medical liquid storage portion 210 is formed of the material that transmits light, so that the surface characteristics of the medical liquid facing region 211*b* may be recognized, and whether the accommodated state and the accommodated amount of the stored medical liquid may be checked.

Although not illustrated, a medical liquid facing region of the second outer portion 212 opposite to the first outer portion 211 may also have a surface-treated region, for example, a plurality of protrusions, a detailed description is omitted because it is the same as that of the first outer portion 211.

Although not illustrated, the above-described FIGS. 6 to 8 may be selectively applied to the present embodiment.

In this embodiment, the medical liquid is stored in the medical liquid storage portion of the apparatus for infusing medical liquid, and the medical liquid stored in the medical liquid storage portion may be delivered to the needle module through the driving portion, and may be infused into the infusion target, specifically, the user's body, over a plurality of times by a desired amount through pumping.

The medical liquid storage portion may include the outer portion, and the medical liquid may be accommodated in the inner space surrounded by the outer portion. The medical liquid facing region, which is the surface of the space facing the medical liquid of the outer portion, may include the protrusion and the space on the surface, for example, may include a region having roughness as it is finely surface-treated.

Through this, it is possible to form a friction force between the inner region of the medical liquid storage portion and the moving portion arranged for pumping and movement of the medical liquid inside the medical liquid storage portion, and it is possible to reduce or prevent unnecessary sliding of the moving portion.

By improving the adhesion properties between the moving portion and the medical liquid facing region, the medical liquid of the medical liquid storage portion may be effectively infused into the needle module, and as a specific example, it is possible to precisely control the infusion of a predetermined medical liquid over a plurality of times.

Through this, it is possible to increase the convenience of the user who uses the apparatus for infusing medical liquid and the effect through infusion of the medical liquid.

In addition, as an optional embodiment, when the medical liquid storage portion is formed of the light-transmitting material, the presence or absence of the medical liquid in the inner space, the remaining amount of the medical liquid, etc. may be easily checked through the shape of the surface of the medical liquid facing region. In addition, by increasing the surface area in contact with the medical liquid in the inner space of the medical liquid storage portion, it is possible to effectively accommodate the medical liquid in the medical liquid storage portion.

Figure 13:
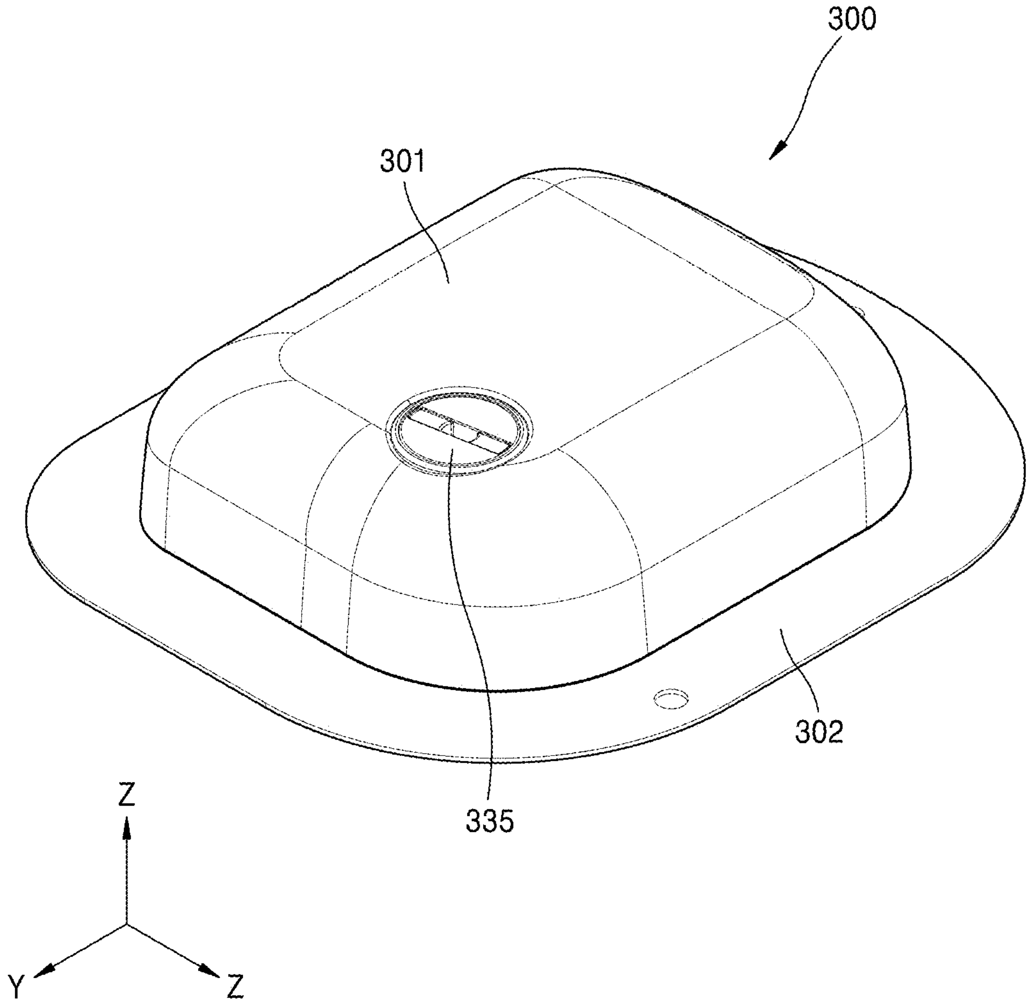
FIG. 13 is a perspective view schematically illustrating an apparatus for infusing medical liquid according to another embodiment of the present disclosure.
Figure 14:
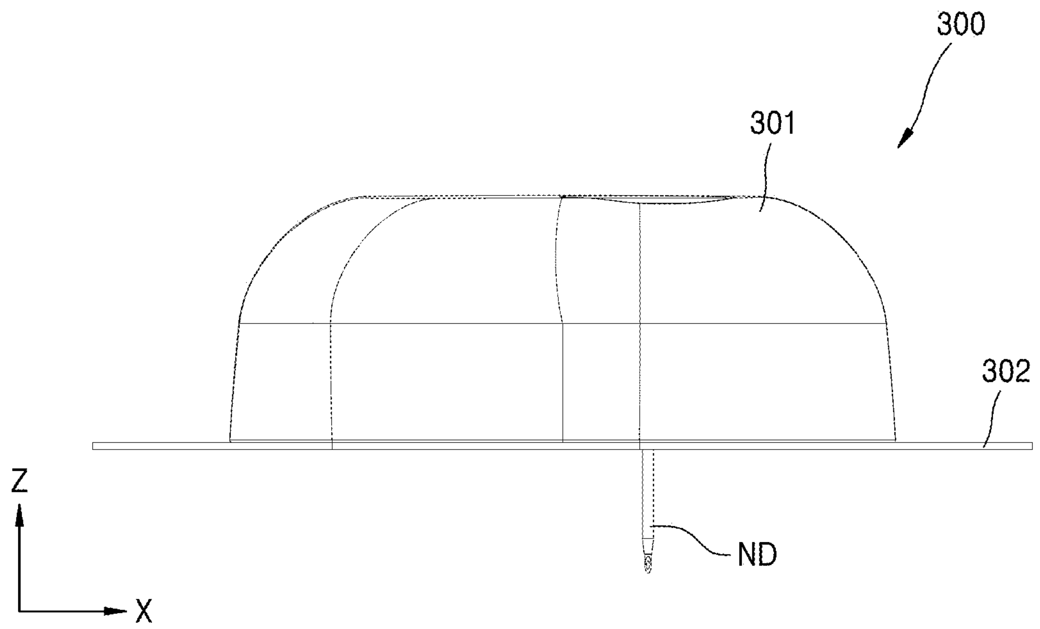
FIG. 14 is a schematic front view of the apparatus for infusing medical liquid of FIG. 13.

FIG. 13 is a perspective view schematically illustrating an apparatus for infusing medical liquid according to another embodiment of the present disclosure, and FIG. 14 is a schematic front view of the apparatus for infusing medical liquid of FIG. 13.

Figure 15:
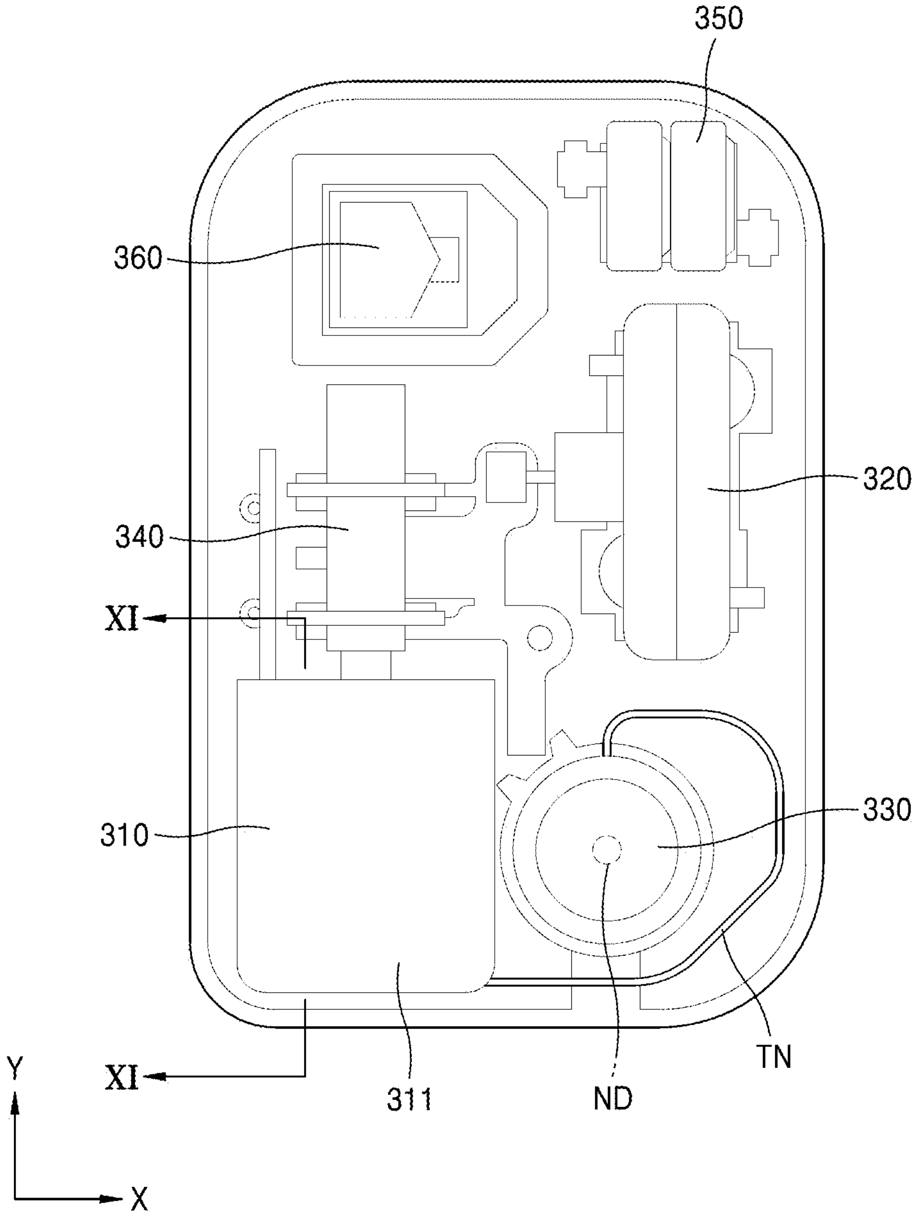
FIG. 15 is a schematic plan view of the apparatus for infusing medical liquid of FIG. 13 with a cover removed for convenience of explanation.
Figure 16:
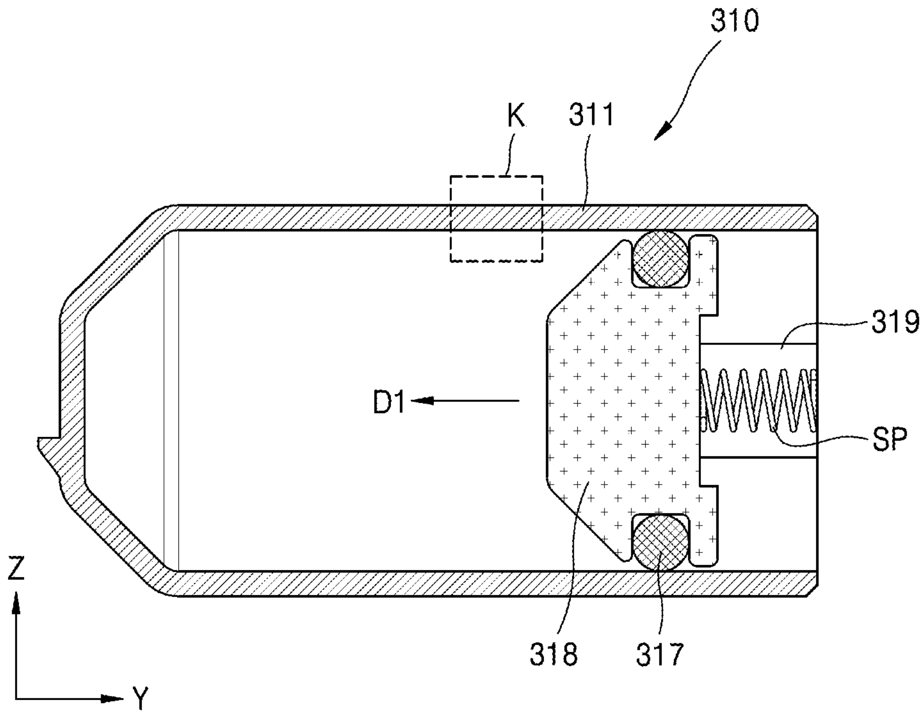
FIG. 16 is a cross-sectional view taken along line XVI-XVI of FIG. 15.
Figure 17:
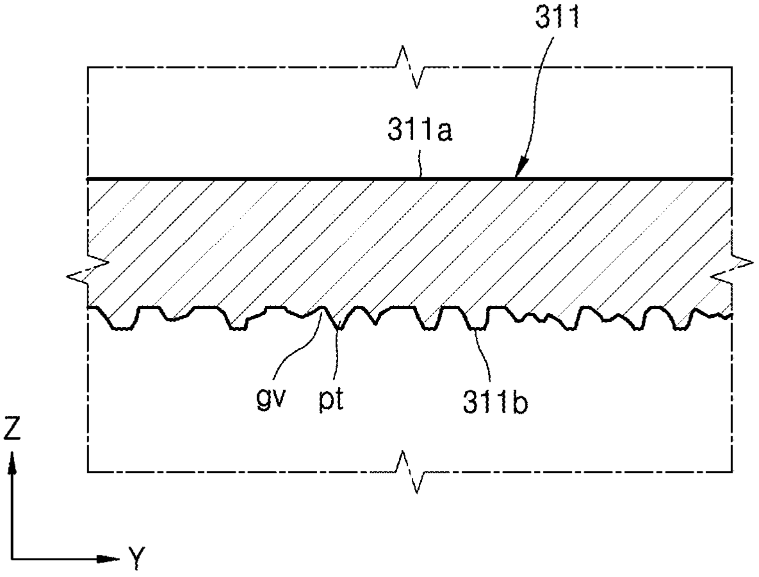
FIG. 17 is an enlarged view of K of FIG. 16.

FIG. 15 is a schematic plan view of the apparatus for infusing medical liquid of FIG. 13 with a cover removed for convenience of explanation, FIG. 16 is a cross-sectional view taken along line XVI-XVI of FIG. 15, and FIG. 17 is an enlarged view of K of FIG. 16.

Referring to FIGS. 13 to 16, an apparatus for infusing medical liquid 300 of this embodiment may include a medical liquid storage portion 310, a driving portion 320 and a needle module 330.

The apparatus for infusing medical liquid 300 may be disposed adjacent to a medical liquid infusion target, for example, a human skin, and may infuse the medical liquid in an infusion direction (Z-axis direction of FIG. 14). Specifically, the medical liquid may be infused through the needle portion ND in the Z-axis direction of FIG. 14.

Also, as an optional embodiment, the apparatus for infusing medical liquid 300 may be mounted on a user's body.

The apparatus for infusing medical liquid 300 may include a cover 301, and the cover 301 may be formed to cover the medical liquid storage portion 310, the driving portion 320 and the needle module 330.

For convenience of explanation, FIG. 15 illustrates a state in which the cover 301 of FIG. 13 is removed.

The apparatus for infusing medical liquid 300 may include a base 302, and the base 302 may be formed to face the cover 301. In addition, as an optional embodiment, the base 302 may include a larger shape than the cover 301, and may be stably attached to the user's body through this.

For example, at least one region of the base 302 may be in close contact with the user's body, and as an optional embodiment, may include an adhesive material, or may include an adhesive tape shape.

As an optional embodiment, the cover 301 and the base 302 may be connected to each other to become a housing of the apparatus for infusing medical liquid 300.

As an optional embodiment, the cover 301 may include an opening, a button 335 is disposed to correspond to the opening, and the button 335 may correspond to the needle module 330.

For example, the button 335 may be disposed on the needle module 330, and the button 335 may be formed so that the user may press or rotate it. Movement with respect to the needle module 330 may be possible through the button 335.

The medical liquid storage portion 310 may be formed to accommodate one or more types of medical liquids. For example, the medical liquid storage portion 310 may accommodate a medical liquid to infuse the medical liquid into a human at one time. Also, as another example, the medical liquid storage portion 310 may accommodate a medical liquid to continuously infuse the medical liquid over a plurality of times.

The medical liquid storage portion 310 may include a tank-shaped container to store medical liquid. The medical liquid storage portion 310 may contain a waterproof material, for example, a plastic-based material, capable of accommodating the medical liquid, and may be formed of various other materials.

In an alternative embodiment, the medical liquid storage portion 310 may contain a glass, metal, or silicon material.

As illustrated in FIG. 16, the medical liquid storage portion 310 includes at least one outer portion 311, and the medical liquid may be accommodated in an inner space formed inside the outer portion 311. For example, the outer portion 311 may be a first outer portion 311 facing the cover 301.

The medical liquid may be of various types, and may include an insulin-based medical liquid for diabetic patients, other medical liquids for pancreas, cardiac medical liquid, and other various types of medical liquid.

As an optional embodiment, the medical liquid storage portion 310 may be replenished with the medical liquid through a charging passage (not illustrated).

A moving portion 390 may be disposed in the inner space of the medical liquid storage portion 310.

For example, at least one moving portion 318 may be disposed in a space in which the medical liquid is accommodated inside the outer portion 311 of the medical liquid storage portion 310.

Such the moving portion 318 may allow the medical liquid to move effectively, and specifically, may allow the medical liquid accommodated in the medical liquid storage portion 310 to be easily delivered to the needle module 330 to be described later.

For example, through the movement of the moving portion 318, the medical liquid stored in the medical liquid storage portion 310 may be infused into the user's body as many times as desired.

The moving portion 318 may be connected to a supporting portion 319, and may move in a moving direction (D1 of FIG. 16), for example, a longitudinal direction of the medical liquid storage portion 310 together with the supporting portion 319.

For efficiency and precision of movement through the supporting portion 319, an elastic portion SP may be disposed, and the elastic portion SP may be in the form of a spring shape.

A middle portion 317 may be disposed to correspond to one region of an outer surface of the moving portion 318, and the middle portion 317 may include an O-ring shape made of a rubber material that may reduce or block a gap between the moving portion 318 and the medical liquid storage portion 310.

As an optional embodiment, a groove is formed in the outer surface of the moving portion 318 to face the inner surface of the medical liquid storage portion 310, and the middle portion 317 may be stably disposed in this groove, through this, the middle portion 317 may effectively move together with the moving portion 318.

As an optional embodiment, the moving portion 318 may have a shape corresponding to the space inside the medical liquid storage portion 310, for example, may have a convex protrusion.

The driving portion 320 may allow the medical liquid stored in the medical liquid storage portion 310 to be delivered to the needle module 330, and to be easily infused from the needle module 330 into the medical liquid infusion target, for example, human skin.

As an optional embodiment, a driving connection portion 340 may be disposed between the driving portion 320 and the medical liquid storage portion 310 to transmit precise driving force for the moving portion 318 of the medical liquid storage portion 310.

For example, the driving connection portion 340 may include at least one gear module.

As an optional embodiment, the driving portion 320 may include a pump, and the medical liquid stored in the medical liquid storage portion 310 may be delivered to the needle module 330 by a predetermined amount through pumping of the pump.

The driving portion 320 may be connected to a power source 350. The power source 350 may include a battery, and may include a rechargeable battery. Also, as another example, the power source 350 may include a disposable battery.

Also, as an optional embodiment, the driving portion 320 may be electrically connected to a controller (not illustrated), and the driving portion 320 may control infusion of the medical liquid through the control of the controller.

All kinds of pumps having a medical liquid suction power and a medical liquid discharge power by electricity may be used for the driving portion 320. For example, all kinds of pumps such as mechanical displacement type micropump and electromagnetic motion type micropump may be used. The mechanical displacement type micropump is a pump that uses the motion of a solid or fluid, such as a gear or diagram, to generate a pressure difference to induce the flow of fluid, and includes a diaphragm displacement pump, a fluid displacement pump, a rotary pump, and the like. The electromagnetic motion type micropump is a pump that directly uses electrical or magnetic energy to move a fluid, and includes a hydrodynamic pump (EHD), an electro osmotic pump, a magneto hydrodynamic pump, an electro wetting pump, and the like.

The needle module 330 may include at least one needle portion ND. The needle portion ND has an empty interior, and the medical liquid of the medical liquid storage portion 310 may be infused into the medical liquid infusion target through this interior space.

A connection portion TN may be disposed between the needle module 330 and a medical liquid storage portion 310. The connection portion TN may include a delivery region such that at least the medical liquid of the medical liquid storage portion 310 is delivered to the needle module 330, for example, may include a hollow tube shape.

The connection portion TN may be formed in various shapes, for example, may include a flexible tube shape.

The driving portion 320 of the present embodiment may be connected to the medical liquid storage portion 310 so that the medical liquid accommodated in the medical liquid storage portion 310 may be easily delivered to the needle module 330 through the connection portion TN.

The needle module 330 may include a holder supporting the needle portion ND, and the holder supporting the needle portion ND may be disposed to face the button 335. Also, although not illustrated, a spring (not illustrated) may be disposed between the needle module 330 and the button 335. The button 335, spring (not illustrated), and the needle module 330 may be aligned along the Z-axis of FIG. 14.

Also, although not illustrated, as an optional embodiment, a sensor portion 360 may be further positioned between the cover 301 and the base 302, or on at least one surface of them.

Such the sensor portion 360 may be provided to sense whether the needle module 330 is adjacent to a needle through hole formed in the base 302.

Also, such the sensor (not illustrated) may be electrically connected to the above-described controller (not illustrated) that controls the driving portion 320.

FIG. 16 is a cross-sectional view taken along line XVI-XVI of FIG. 15, and FIG. 17 is an enlarged view of K of FIG. 16.

Referring to FIGS. 16 and 17, the inner space of the medical liquid storage portion 310 is illustrated. The inner space of the medical liquid storage portion 310 may be defined as an inner space of outer portion 311.

The moving portion 318 may be disposed in the inner space corresponding to the outer portion 311 of the medical liquid storage portion 310, and the moving portion 318 has been described above.

The moving portion 318 may move toward a discharge port (not illustrated) along the longitudinal direction D1 of the medical liquid storage portion 310 in the inner space of the medical liquid storage portion 310, and this discharge port (not illustrated) may be connected to the needle module 330.

Referring to FIG. 17, the first outer portion 311 may include an outer surface region 311*a* and a medical liquid facing region 311*b*.

The outer surface region 311*a* may correspond to an outer surface of the first outer portion 311, and the medical liquid facing region 311*b* may define the inner space in which the medical liquid of the medical liquid storage portion 310 is accommodated, and may face the medical liquid at least in one region and contact the medical liquid at least at one time point.

The medical liquid facing region 311*b* may include a surface-treated region. As an optional embodiment, the medical liquid facing region 311*b* may include one or more protrusions pt and spaces gv adjacent thereto. For example, the medical liquid facing region 311*b* may include a plurality of protrusions pt, and spaces gv may be formed between adjacent protrusions pt.

As an optional embodiment, the protrusion pt may include a plurality of protrusions pt having different sizes and shapes.

The medical liquid facing region 311*b* has the surface-treated region, for example, the region including the plurality of protrusions pt, so that when the medical liquid storage portion 310 is made of a material that transmits at least light, and when the medical liquid is accommodated in the medical liquid storage portion 310, a surface shape of the medical liquid facing region 311*b* may be recognized, and through this, it is possible to easily determine whether the medical liquid is accommodated or the accommodated amount.

In addition, the medical liquid facing region 311*b* may have the surface-treated region, for example, the region including the plurality of protrusions pt to increase the surface area so that the medical liquid is more efficiently accommodated in the medical liquid storage portion 310.

In addition, the friction force and adhesion between the moving portion 318 for easy delivery of the medical liquid accommodated in the medical liquid storage portion 310 and the medical liquid facing region 311*b* may be improved.

As a specific example, the friction force and adhesion between the middle portion 317 disposed on the outer surface of the moving portion 318 and the medical liquid facing region 311*b* may be improved.

Through this, when the moving portion 318 moves, the medical liquid may be effectively delivered from the medical liquid storage portion 310 to the needle module 330 as precisely as desired.

The protrusion pt may be formed in a fine shape so that unnecessary residual of the medical liquid is reduced, and damage or unnecessary interference to the moving portion 318 that may be disposed therein is reduced.

For example, the size of the protrusion pt may be several micrometers or less, and specifically, it may be 0.1 to 10 micrometers.

Through this, the medical liquid facing region 311*b* may have a surface roughness value, for example, a roughness value of 0.1 to 5 micrometers, and specifically, a roughness value of 0.2 to 1 micrometers.

The medical liquid facing region 311*b* may be formed to include the plurality of protrusions pt by various methods, for example, may be formed by treating the surface by a physical method or may be formed by a method using a chemical solution.

As an optional embodiment, the outer surface region 311*a* and the medical liquid facing region 311*b* may have different surface shapes.

For example, the outer surface region 311*a* and the medical liquid facing region 311*b* may have different roughness. As a specific example, the outer surface region 311*a* and the medical liquid facing region 311*b* may have different surface roughness.

As an optional embodiment, the value of the surface roughness of the medical liquid facing region 311*b* may be greater than the value of the surface roughness of the outer surface region 311*a*.

Through this, the medical liquid storage portion 310 is formed of the material that transmits light, so that the surface characteristics of the medical liquid facing region 311*b* may be recognized, and whether the accommodated state and the accommodated amount of the stored medical liquid may be checked.

Although not illustrated, the medical liquid facing region 311*b* may be formed on the inner surface of the medical liquid storage portion 310 to correspond to the region in which at least the moving portion 318 moves or the region in which the middle portion 317 moves.

Although not illustrated, the above-described FIGS. 6 to 8 may be selectively applied to the present embodiment.

Figure 18:
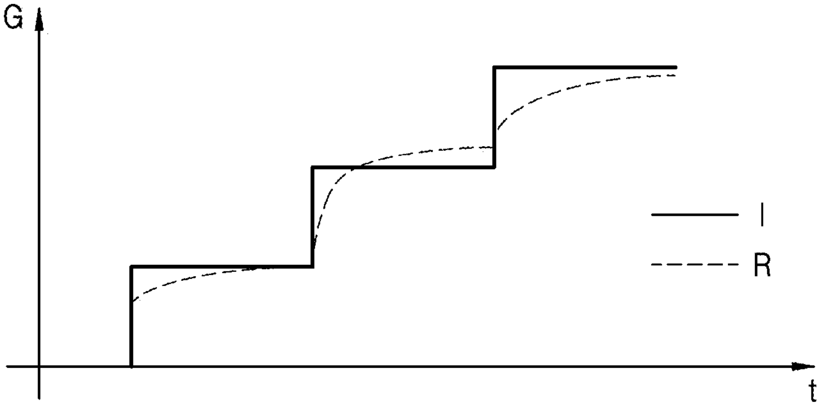
FIG. 18 is an exemplary view for explaining a process of infusing the medical liquid using the apparatus for infusing medical liquid of the present embodiment.

FIG. 18 is an exemplary view for explaining a process of infusing the medical liquid using the apparatus for infusing medical liquid of the present embodiment.

Referring to FIG. 18, a horizontal axis represents time t and a vertical axis represents an infusion amount of medical liquid G.

After the apparatus for infusing medical liquid in one of the above-described embodiments is mounted on a user's body, the necessary medical liquid may be infused multiple times.

For example, as illustrated in FIG. 18, it may have a design value (line I) to infuse multiple times (3 times in FIG. 18).

A difference may occur between an actual value (line R) of the medical liquid in the medical liquid storage portion delivered to the needle module by the driving portion and infused into the user's body, as illustrated in FIG. 18.

In this embodiment, the medical liquid is stored in the inner space of the medical liquid storage portion of the apparatus for infusing medical liquid, and a surface with increased roughness by increasing the surface roughness value through surface treatment, etc. may be formed on the surface of the inner space in which the medical liquid is stored.

Through this, the precision of injection of the medical liquid may be improved, for example, the delivery of the medical liquid to the needle module through the movement of the moving portion disposed inside the medical liquid storage portion is effectively progressed, so that delays or omissions of delivery of the medical liquid may be reduced or prevented.

As a result, the medical liquid injection characteristic is secured to be close to the design value (line I in FIG. 18), the convenience of the user equipped with the apparatus for infusing medical liquid may be improved, and the medicinal effect of the medical liquid through the medical liquid infusion may be increased.

In this embodiment, the medical liquid is stored in the medical liquid storage portion of the apparatus for infusing medical liquid, and the medical liquid stored in the medical liquid storage portion may be delivered to the needle module through the driving portion, and may be infused into the infusion target, specifically, the user's body, over a plurality of times by a desired amount through pumping.

The medical liquid storage portion may include the outer portion, and the medical liquid may be accommodated in the inner space surrounded by the outer portion. The medical liquid facing region, which is the surface of the space facing the medical liquid of the outer portion, may include the protrusion and the space on the surface, for example, may include a region having roughness as it is finely surface-treated.

Through this, it is possible to form a friction force between the inner region of the medical liquid storage portion and the moving portion arranged for pumping and movement of the medical liquid inside the medical liquid storage portion, and it is possible to reduce or prevent unnecessary sliding of the moving portion.

By improving the adhesion properties between the moving portion and the medical liquid facing region, the medical liquid of the medical liquid storage portion may be effectively infused into the needle module, and as a specific example, it is possible to precisely control the infusion of a predetermined medical liquid over a plurality of times. In addition, the gap between the middle portion disposed on the outer surface of the moving portion to improve adhesion in the medical liquid storage portion and the medical liquid facing region is reduced or blocked, so that a precise control characteristic for infusion of a desired precise medical liquid may be improved.

Through this, it is possible to increase the convenience of the user who uses the apparatus for infusing medical liquid and the effect through infusion of the medical liquid.

In addition, as an optional embodiment, when the medical liquid storage portion is formed of the light-transmitting material, the presence or absence of the medical liquid in the inner space, the remaining amount of the medical liquid, etc. may be easily checked through the shape of the surface of the medical liquid facing region. In addition, by increasing the surface area in contact with the medical liquid in the inner space of the medical liquid storage portion, it is possible to effectively accommodate the medical liquid in the medical liquid storage portion.

As such, the present disclosure has been described with reference to the embodiments shown in the drawings, which are merely exemplary, and those of ordinary skill in the art will understand that various modifications and equivalent other embodiments are possible therefrom. Accordingly, the true technical protection scope of the present disclosure should be determined by the technical spirit of the appended claims.

INDUSTRIAL APPLICABILITY

The specific implementations described in the embodiment are only embodiments, and do not limit the scope of the embodiment in any way. For brevity of the specification, descriptions of conventional electronic components, control systems, software, and other functional aspects of the systems may be omitted. In addition, the connection or connection members of lines between the components shown in the drawings illustratively represent functional connections and/or physical or circuit connections, and in an actual device, various functional connections, physical connections that are replaceable or additional may be referred to as connections, or circuit connections. In addition, unless there is a specific reference such as "essential", "importantly", etc., it may not be a necessary component for the application of the present disclosure.

In the specification of the embodiments (especially in the claims), the use of the term "above" and similar referential terms may be used in both the singular and the plural. In addition, when a range is described in the embodiment, it includes the disclosure of applying individual values within the range (unless there is a description to the contrary), and each individual value constituting the range is described in the detailed description. Finally, the steps constituting the method according to the embodiment may be performed in an appropriate order unless the order is explicitly stated or there is no description to the contrary. The embodiments are not necessarily limited according to the description order of the steps. The use of all examples or illustrative terms (eg, etc.) in the embodiments is merely for the purpose of describing the embodiments in detail. Accordingly, the scope of the embodiments is not limited by the examples or exemplary terms, unless limited by the claims. In addition, those skilled in the art will recognize that various modifications, combinations, and changes can be made in accordance with design conditions and factors within the scope of the appended claims or their equivalents.

The invention claimed is:

1. An apparatus for infusing medical liquid, the apparatus comprising:

a needle module having at least one needle portion configured to be injected into a user's body;

a medical liquid storage portion having an inner space to store medical liquid delivered to the needle module, wherein an inner surface of the inner space includes a surface-treated shape, the surface-treated shape of the inner surface including a region including a plurality of protrusions;

a driving portion connected to the medical liquid storage portion to transfer the medical liquid of the medical liquid storage portion to the needle module;

at least one moving portion for moving the medical liquid disposed in the inner space of the medical liquid storage portion, the at least one moving portion including a groove formed to face the surface-treated shape of the inner surface; and a middle portion disposed in the groove of the at least one moving portion to face the surface-treated shape of the inner surface, wherein the surface-treated shape of the inner surface has the same material as the inner surface of the medical liquid storage portion and is integrated with the inner surface of the medical liquid storage portion, wherein an injection direction of the medical liquid through the at least one needle portion and a movement direction of the at least one moving portion intersect with each other, and wherein the driving portion includes a pump.

2. The apparatus of claim 1, wherein the inner surface of the inner space of the medical liquid storage portion and an outer surface of the medical liquid storage portion have different surface shapes from each other.

3. The apparatus of claim 1, wherein a roughness value of the inner surface of the inner space of the medical liquid storage portion is different from a roughness value of an outer surface of the medical liquid storage portion.

4. The apparatus of claim 3, wherein the roughness value of the inner surface of the inner space of the medical liquid storage portion is greater than the roughness value of the outer surface of the medical liquid storage portion.

5. The apparatus of claim 1, further comprising a cover portion formed to cover the medical liquid storage portion, the needle module and the driving portion.

* * * * *